United States Patent [19]

Ghaerzadeh

[11] Patent Number: 5,342,303
[45] Date of Patent: Aug. 30, 1994

[54] BALLOON CATHETERS, SCOPES AND RELATED MEDICAL DEVICES HAVING NON-OCCLUDING BALLOON INFLATION-DEFLATION APERTURES

[75] Inventor: Kambiz Ghaerzadeh, Costa Mesa, Calif.

[73] Assignee: Baxter International Inc., Deerfield, Ill.

[21] Appl. No.: 132,603

[22] Filed: Oct. 6, 1993

[51] Int. Cl.$^5$ .............................................. A61M 29/00
[52] U.S. Cl. .................................. 604/96; 604/99; 606/192
[58] Field of Search ............... 604/96, 97–103, 604/52, 53, 49; 606/192–194

[56] References Cited

U.S. PATENT DOCUMENTS

| | | | |
|---|---|---|---|
| 4,931,036 | 6/1990 | Kanai et al. | 604/99 X |
| 5,167,239 | 12/1992 | Cohen et al. | 604/96 X |
| 5,213,576 | 5/1993 | Abiuso et al. | 604/96 |
| 5,226,880 | 7/1993 | Martin | 604/99 |

Primary Examiner—John D. Yasko
Attorney, Agent, or Firm—Stetina & Brunda

[57] ABSTRACT

Non-occluding balloon inflation-deflation aperture(s) which may be formed in any medical catheter, scope or other device having an inflatable formed thereon. In a preferred embodiment, the non-occluding aperture(s) are configured to include at least one angular corner. Specific configurations in which the non-occluding apertures of the invention may be formed include wedge-shaped configurations, generally rectangular configurations, trapezoidal configurations and/or round-concave configurations having angular sub-notches formed therein.

16 Claims, 4 Drawing Sheets

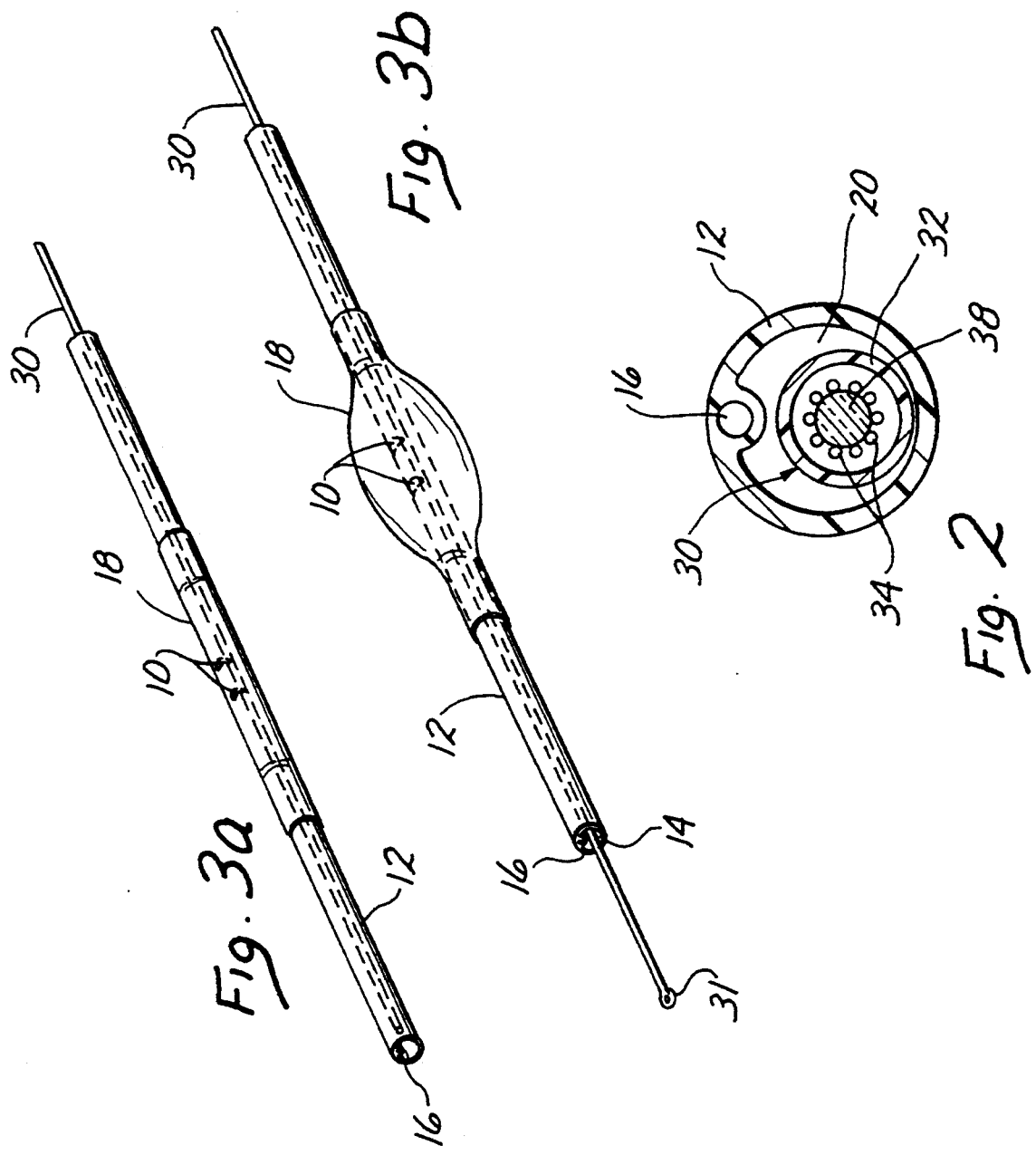

BALLOON CATHETERS, SCOPES AND RELATED MEDICAL DEVICES HAVING NON-OCCLUDING BALLOON INFLATION-DEFLATION APERTURES

FIELD OF THE INVENTION

The present invention relates generally to medical equipment and more particularly improved structural configurations and constructions of catheters, scopes and other devices having inflatable balloons disposed thereon.

BACKGROUND OF THE INVENTION

Many medical devices utilize inflatable balloons for purposes of anchoring, positioning, or therapeutic dilation of surrounding anatomical structures. In some devices, the inflatable balloons are formed of generally rigid non-deformable material which substantially resists untoward deformation when in an inflated state. Other devices do, however, incorporate balloons which are formed of relatively soft, deformable material, such as synthetic rubber or latex.

One problem which may be encountered in some catheters, scopes and other devices having deformable balloons is inadvertent blockage of the balloon inflation/deflation aperture due to compression or collapse of the balloon against the outer surface of the catheter during use. Such blockage of the balloon inflation/deflation aperture typically arises when one side of the inflated balloon becomes compressed against the inflation/deflation aperture through which the balloon is routinely inflated and deflated. Such compression of the balloon may result in plugging of the inflation/deflation aperture such that the balloon may not be volitionally deflated. The inability to volitionally deflate the balloon may result in significant clinical consequences of emergency nature.

In view of the potential for inadvertent blockage of the balloon inflation/deflation aperture in some catheters, scopes or other medical devices there exists a need in the art for the development of new means of constructing such catheters, scopes and other devices so as to minimize or prevent the likelihood of inadvertent blockage of the balloon inflation/deflation aperture during use.

SUMMARY OF THE INVENTION

The present invention generally comprises an improved high seal force configuration for balloon inflation apertures in catheters, scopes and other medical devices having deformable balloons formed thereon.

In accordance with the invention, there are provided catheters, scopes and other medical devices having deformable balloons formed thereon and having one or more balloon inflation-deflation aperture, the configuration(s) of which include at least one angular corner to deter the balloon from fully blocking or occluding said balloon inflation-deflation aperture. Such non-occluding balloon inflation-deflation aperture(s) of the present invention are sized and positioned to provide fluid communication between a balloon inflation-deflation lumen extending through the body of the catheter, scope or other medical device and the interior of the deformable balloon formed thereon.

In accordance with one embodiment of the invention, the balloon inflation-deflation aperture(s) may be in the form of a wedge-shaped notch. Such wedge-shaped notch is preferably cut into the sidewall of the catheter, scope or other medical device so as to provide fluidic communication between a balloon inflation-deflation lumen which extends at least partially through the catheter, scope or other device, and the interior of an inflatable balloon formed thereon.

In accordance with other embodiments of the invention, the non-occluding balloon inflation-deflation aperture(s) may be configured in various other geometric shapes or configurations which have at least one corner formed therein, including but not limited to rectangular notches, trapezoidal notches and/or generally round concave notches having one or more angular or wedge-shaped sub-notches extending therefrom.

Further objects and advantages of the invention will become apparent to those skilled in the art upon reading and understanding of the following detailed description and the accompanying drawings.

BRIEF DESCRIPTION OF THE DRAWINGS

FIG. 2 is a cross-sectional view of the device shown in FIG. 1, through line 2—2.

FIG. 3a is a perspective view of the angioscope portion of the device shown in FIG. 1, with its balloon in a deflated state.

FIG. 3b is a perspective view of the distal portion of the angioscope shown in FIG. 1, with its balloon in an inflated state.

DETAILED DESCRIPTION OF THE PREFERRED EMBODIMENT

Figure 1:
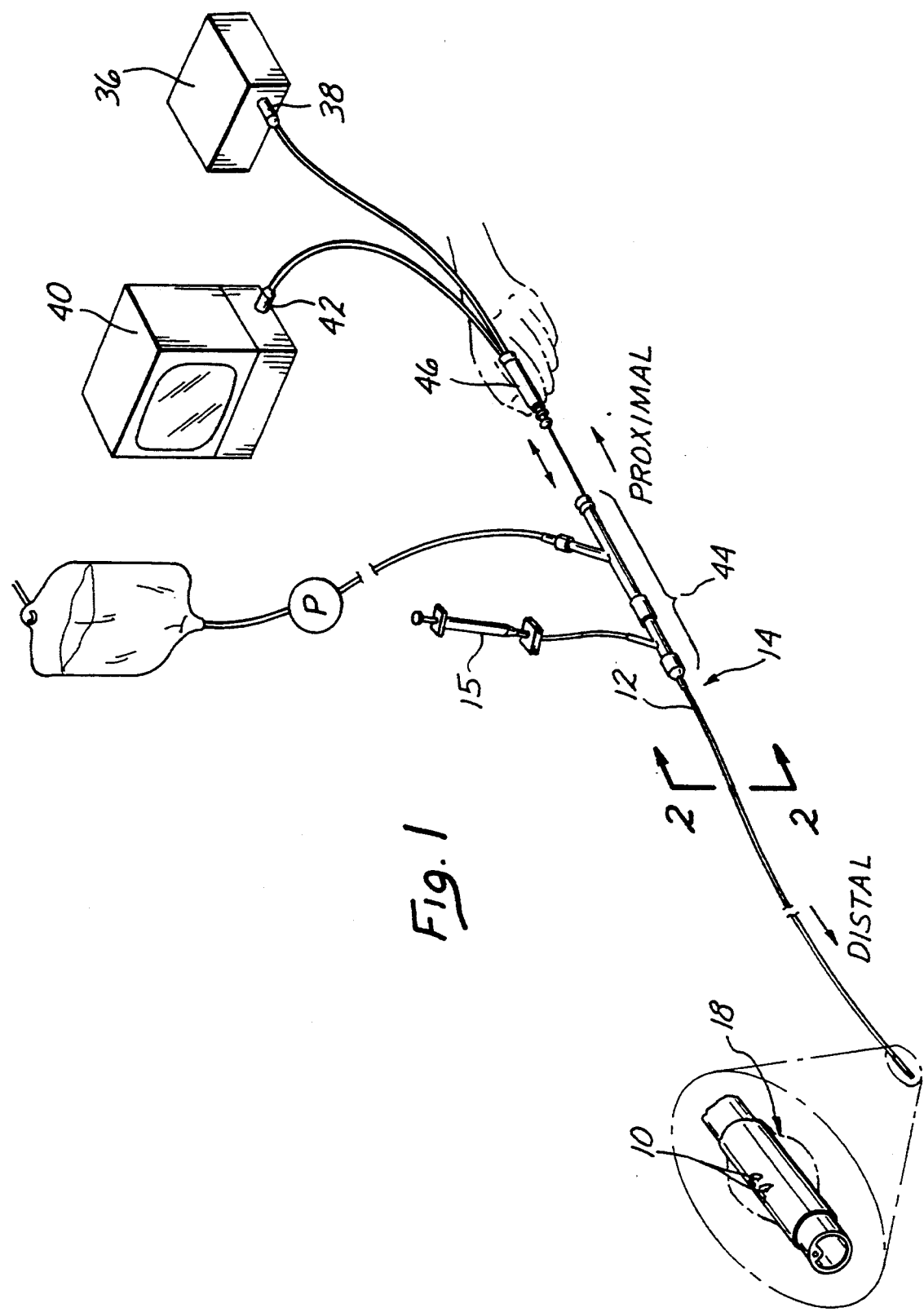
FIG. 1 is a perspective view of an angioscope device including an enlarged breakout view of the distal portion of the catheter body of the device incorporating non-occluding balloon inflation apertures of the present invention.

The following detailed description and the accompanying drawings are provided for purposes of describing and illustrating certain presently preferred embodiments of the invention, and are not intended to limit the scope of the invention in any way.

Although the non-occluding apertures of the present invention are shown in the drawings in connection with specific types of devices (e.g., an angioscope), it is to be appreciated and understood that the non-occluding apertures of the present invention may be utilized in many different types of medical devices, including various catheters (e.g., Swan-Gantz right heart catheters), scopes (e.g., angioscopes) and other instruments or apparatus upon which deformable balloons are disposed.

Irrespective of what type of device (e.g., catheter, scope, etc. . . .) the invention is incorporated in, the invention comprises one or more inflation/deflation apertures shaped and configured so as to avoid total blockage of the aperture(s) in the event that the balloon becomes collapsed or compressed against the adjacent outer surface of the device (e.g., catheter, scope, etc. . . .)

One example of a device which incorporates the non-occluding balloon inflation/deflation aperture(s) 10 of the present invention is the angioscope 14 shown in FIG. 1–3. In such angioscope 14, the non-occluding apertures 10 of the present invention comprise angular slits formed in the sidewall of the elongate catheter body 12 of the angioscope 14. Such non-occluding apertures 10 permit balloon inflation fluid (such as carbon dioxide gas or a radiographic contrast liquid) to be infused by syringe 15 distally through balloon inflation lumen 16 to inflate the balloon 18 and, subsequently to be withdrawn proximally by syringe 15 through lumen 16 to deflate said balloon 18.

The deformable balloon 18 is disposed, mounted or affixed on the outer surface of the catheter body 12. In the embodiment shown, the balloon comprises a cylindrical segment of elastic rubber fused at either end to the outer surface of the catheter body and having a mid-section which is free of said catheter body so as to be radially inflatable in the manner shown. Such deformable balloon 18 is formed of relatively soft elastic material such as polyurethane, silicone, synthetic rubber, or latex (e.g., Kraton ™ synthetic rubber, Shell Chemical Company, Oak Brook, Ill.).

An endoscopic component 30 is disposed longitudinally within the working lumen 14 of the catheter body 12. Endoscopic component 30 comprises an elongate tubular sheath 32 preferably formed of flexible metal or plastic material. Ten(10) illuminating optical fibers 34 extend longitudinally through sheath 32 and terminate at the distal end thereof to carry illuminating light through the length of the endoscopic component 30. The proximal ends of illuminating optical fiber bundles 34 are connectable to an external illuminator or light source 36 by way of connector 38. Illuminator or light source 36 may then be utilized by the operator to pass illuminating light through the illuminating fiber bundles 34 of the endoscopic component 30 to the distal end thereof.

An optical image receiving optical fiber bundle 38 also extends longitudinally through the outer sheath 32 of the endoscopic component 30. The proximal end of optical image receiving fiber bundle 38 is connectable by way of connector 42 to an external image displaying system 40, such as a camera (e.g., Model OPTX-3000, Baxter Healthcare Corporation, Deerfield, Ill.) and video monitor (e.g., Model DVM-1343-MD, Sony, Inc.) of the type typically utilized for displaying endoscopic images in clinical applications.

A handle 46 is formed on the proximal end of the endoscopic component 30. The endoscopic component 30 is inserted axially through proximal connector assembly 44 and abuts annularly against a seal or O-ring within proximal connector assembly 44 so as to prevent fluid backflow through working lumen 14. The endoscopic component 30 is longitudinally advanceable and retractable as indicated by the arrows on FIG. 1. As such, the endoscopic component 30 may be advanced in a distal direction such that the distal end thereof advances forward of the distal end of the catheter body 12. In coronary artery applications, it is preferable that the distal end of the endoscopic component be advanceable to a fully extended point approximately 3–5 cm beyond the distal end of the catheter body 12. Alternatively, the endoscopic component 30 may be retracted in the proximal direction to a point where the endoscopic component 30 is withdrawn into the working lumen 14 of the catheter body 12, such that tip member 31 of the endoscopic component 30 is in contact or abutment with the distal end of the catheter body 12.

Figure 4A:
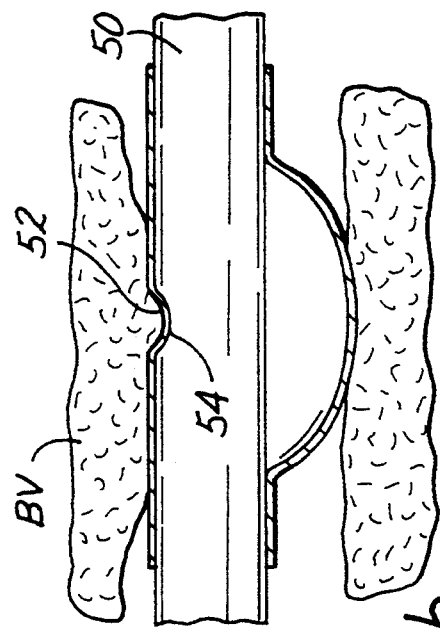
FIG. 4a is a longitudinal sectional view of a prior art device having an inflated deformable balloon is disposed within a blood vessel.
Figure 4B:
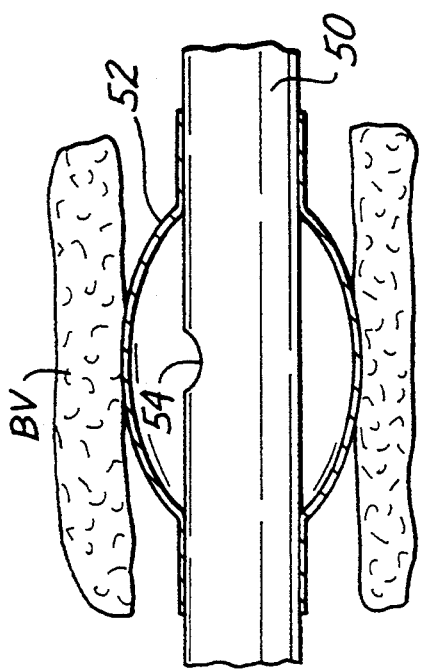
FIG. 4b is a longitudinal sectional view of the prior art device of FIG. 4a wherein the inflated balloon has become deformed in a manner which results in blockage of the balloon inflation/deflation aperture of the device.

The advantages afforded by the non-occluding balloon inflation apertures 10 of the present invention may be clearly appreciated upon consideration of the illustrations of FIGS. 4a–4b. FIGS. 4a–4b show a prior art catheter device 50 having a deformable inflatable balloon 52 disposed on the outer surface thereof. A single balloon inflation lumen (not shown) extends longitudinally through the catheter body 50. A single generally round balloon inflation-deflation aperture 54 extends through the wall of the catheter body 50 to provide fluidic communication between the single balloon inflation (not shown) and the interior of balloon 52. In the illustrations of FIGS. 4a–4b the catheter 50 is disposed within a blood vessel BV. In the showing of Figure a, the balloon is properly inflated in a non-deformed, annular configuration. In such state, the balloon inflation aperture 54 remains non-occluded and capable of withdrawing balloon inflation fluid from the interior of the balloon 52. However, as shown in FIG. 4b, the wall of blood vessel BV may inadvertently cause compression on one side of the balloon 52 so as to collapse or compress the balloon 52 against the balloon inflation-deflation aperture 54. In this state (FIG. 4b), withdrawal of balloon inflation fluid from balloon 52 may be blocked by balloon 52 and, thus, the balloon 52 cannot be fully deflated by the operator and a potentially serious clinical situation has been created as a result of such inadvertent non-deflation of balloon 52.

The non-occluding balloon inflation apertures 10 of the present invention are specifically configured to overcome the problem of inadvertent balloon non-deflation due to blockage of the balloon inflation-deflation aperture by the balloon itself, as shown in the illustration of FIG. 4b.

The non-occluding aperture or apertures 10 of the present invention are configured in other than a circular or round configuration so that the pliable material of the balloon 18 is prevented or deterred from fully collapsing into and plugging or blocking the aperture(s) 10. Furthermore, certain configurational aspects and/or angular disposition of the non-occluding aperture 10 of the present invention are specifically pre-determined such that, even when the balloon 18 is fully collapsed against the aperture 10, the flaccid non-inflated material of the balloon 18 will not fully block or occlude the aperture 10.

Figure 5A:
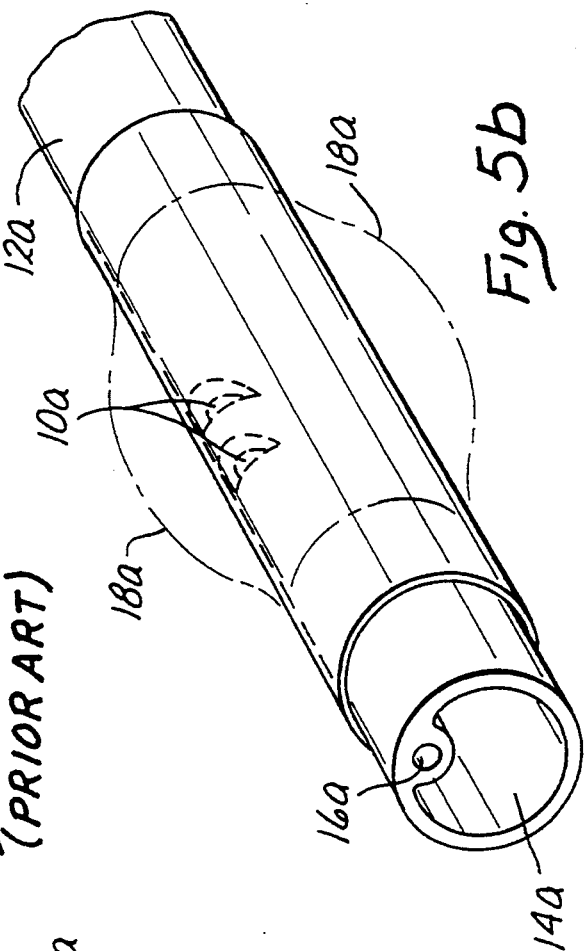
FIG. 5a is a partial perspective view of a device incorporating the non-occluding balloon inflation apertures of the present invention.
Figure 5B:
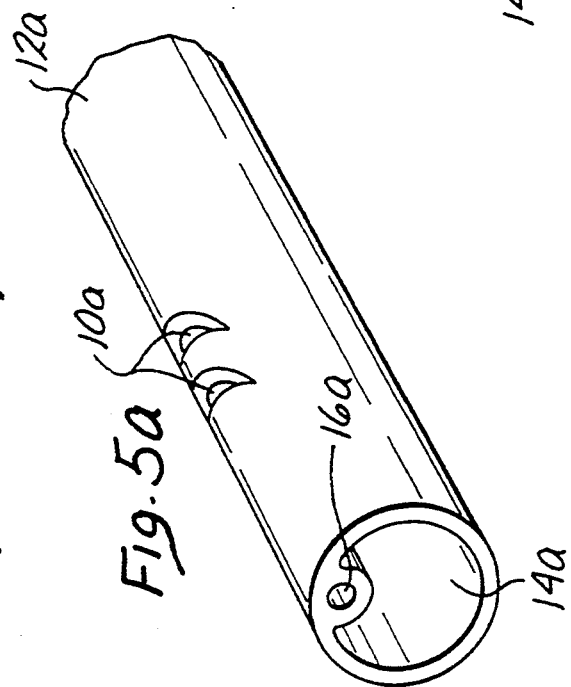
FIG. 5b is a perspective showing of the device of FIG. 5a having an inflated, deformable balloon shown in conjunction therewith (phantom lines).
Figure 5C:
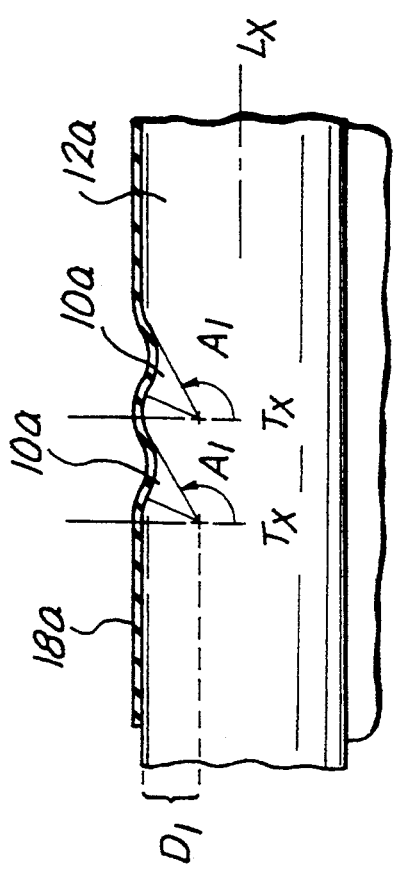
FIG. 5c is a longitudinal sectional view of a portion of the device of FIG. 5b, showing the balloon in a deflated condition.

In the embodiment of the invention shown in FIGS. 5a, 5b and 5c, the non-occluding apertures 10a of the present invention comprise angular wedge-shaped notches formed or cut in the wall of a catheter or device body 12a so as to provide fluidic communication between the balloon inflation lumen 16a and the interior of balloon 18a.

With specific reference to FIG. 5c, each angular wedge-shaped notch 10a is preferably disposed at an angle A1 relative to transverse axes Tx of the catheter 12a. Each such transverse axis $T_x$ extends perpendicular to the longitudinal axis $L_x$ of the catheter 12a. In devices (e.g., catheters, scopes, etc.) having a balloon inflation lumen 16 with an inner diameter in the range of 0.010–0.012 inches and wall thickness WT in the range of 0.002–0.004 inches, the angle A1 of each angular wedge-shaped notch 10a will typically be in the range of 22–51 degrees and preferably about 37 degrees while the depth $D_1$ of each such angular wedge-shape notch 10a will typically be in the range of 0.006–0.010 inches and preferably about 0.008 inches. By such sizing and angular configuration of the wedge-shaped notches 10a, the material of balloon 18a is prevented or deterred from fully occluding or blocking each such wedge-shaped notch 10a even though the material of the balloon 11a is collapsed against the adjacent surface of catheter body 12a.

Although the presently preferred configuration of the non-occluding apertures 10 of the present invention constitutes the angular wedge-shaped notches 10a shown in FIGS. 5a–5c, it will be appreciated that various other configurations and/or angular dispositions may be utilized within the spirit and scope of the present invention.

Figure 6A:
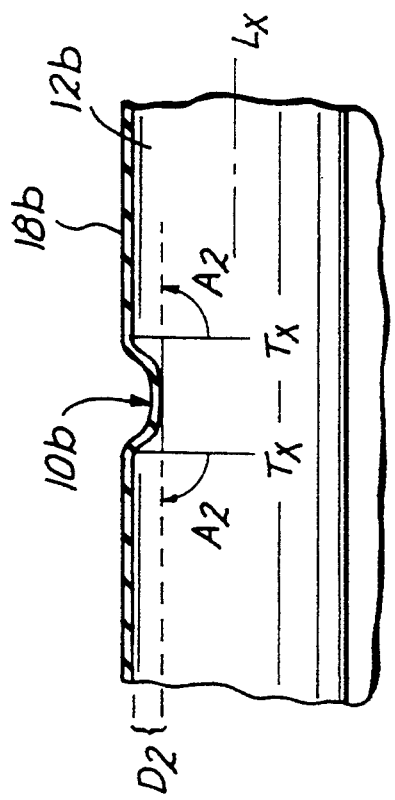
FIG. 6a is a partial longitudinal sectional view of a device incorporating a first alternative embodiment of a non-occluding balloon inflation/deflation aperture of the present invention.
Figure 6C:
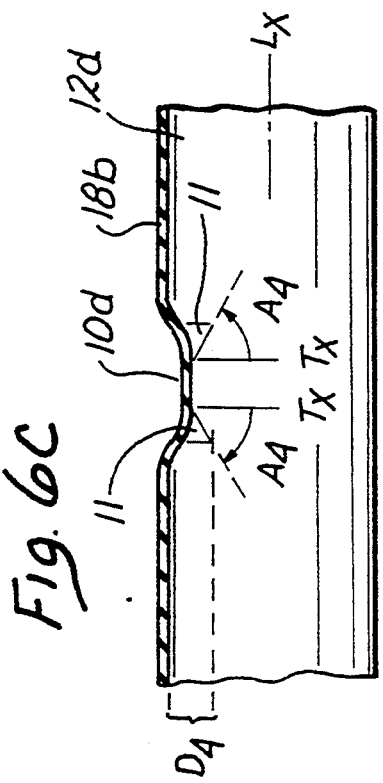
FIG. 6c is a partial longitudinal sectional view of a device incorporating a third alternative embodiment of a non-occluding balloon inflation/deflation aperture of the present invention.
Figure 6B:
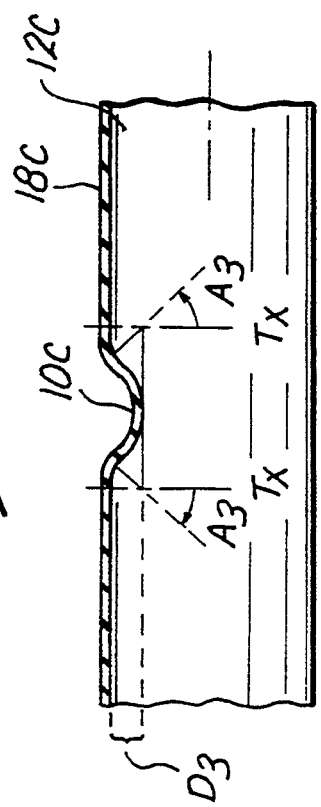
FIG. 6b is a partial longitudinal sectional view of a device incorporating a second alternative embodiment of a non-occluding balloon inflation/deflation aperture of the present invention.

Examples of alternative configurations of non-occluding apertures 10b, 10c, 10d of the present invention are showing FIGS. 6a, 6b and 6c respectively.

As shown in FIG. 6a, one alternative configuration of a non-occluding aperture 10b of the present invention is generally rectangular. The corners of the rectangular aperture form angles A2 which are approximately 90 degrees. The depth D2 of the rectangular non-occluding aperture 10b is sufficient such that the balloon 18b will not fully block the corners of the rectangular non-occluding aperture 10b even when the balloon 18b is collapsed against the aperture 10b. As such, the rectangular non-occluding aperture 10b shown in FIG. 6a is unlikely to become fully closed off or occluded by the material of balloon 18b, thereby minimizing the likelihood of inadvertent failure-to-deflate of the balloon 18b during use.

In the alternative embodiment showing FIG. 6b, the non-occluding aperture 10c is in the form of a partial trapezoid such that the angle A3 formed by the sides of such trapezoidal aperture 18c, relative to transverse axes $T_x$ of the catheter 12c, is preferably in the range of 22–51 degrees. The depth D3 and angular disposition A3 of such trapezoidal non-occluding aperture 10c is such that the balloon 18c will not fully block or occlude the corners of such trapezoidal aperture 10c even when balloon 18c is fully collapsed against the aperture 10c. As such, the trapezoidal aperture 10c is unlikely to become fully blocked by the material of balloon 18c, thereby minimizing the likelihood of inadvertent failure-to-deflate during use.

In the alternative embodiment shown in FIG. 6c, the non-occluding aperture 10d comprises a standard radial or round notch having triangular or wedge shaped sub-notches formed in the base thereof. Such triangular or wedge shaped sub-notches form angles A4 relative to transverse axes $T_x$ of the catheter 12d. It is preferable that such angles A4 be in the range of 40–50 degrees. The depth D4 of the non-occluding aperture 10d shown in FIG. 6c is preferably in the range of 0.006–0.010 inches. The depth D4 and configuration of aperture 10d having sub-notches 11 is such that the material of the balloon 18d will not fully block or occlude the aperture 10d even when the balloon 18d is fully collapsed against the aperture 10d. Thus, the utilization of the non-occluding aperture 10d with subnotches 11 shown in FIG. 6c will minimize the likelihood of inadvertent failure-to-deflate of the balloon 18d during use.

Although the invention has been described herein with specific reference to presently preferred embodiments thereof, it will be appreciated that various additions, modifications, deletions and alterations may be made to the herein described preferred embodiments without departing from the spirit and scope of the invention. For example, one could form a flat or convex cross member(s) or grate over a typical concave round or radiused balloon inflation-deflation aperture of the prior art such that said cross member(s) or grate would prevent the balloon from fully blocking or occluding the balloon inflation-deflation aperture. Accordingly, it is intended that all reasonably foreseeable additions, deletions, alterations and modifications be included within the scope of the invention as defined in the following claims.

What is claimed is:

1. An elongate catheter device having an inflatable balloon mounted thereon, said device comprising:
    a. an elongate catheter body having a proximal end, a distal end, and an outer surface;
    b. at least one balloon inflation-deflation lumen extending longitudinally through at least a portion of said catheter body;
    c. an inflatable balloon mounted on said elongate catheter body at a location between the proximal end, distal ends thereof;
    d. a balloon inflation-deflation aperture to permit flow of balloon inflation flow of balloon inflation fluid between said balloon inflation-deflation lumen and said balloon;
    e. said balloon inflation-deflation aperture having at least one angular corner formed therein to deter said balloon from fully blocking said balloon inflation-deflation aperture.

2. The device of claim 1 wherein said balloon inflation-deflation aperture comprises at least one generally wedge-shaped notch.

3. The device of claim 1 wherein said balloon inflation-deflation aperture comprises two generally wedge-shaped notches.

4. The device of claim 2 wherein said catheter body has a longitudinal axis extending longitudinally therethrough and a transverse axis extending transversely through each generally wedge-shaped notch, each said transverse axis being perpendicular to said longitudinal axis, and further wherein:
    each said generally wedge-shaped notch is disposed at an angle relative to the transverse catheter axis extending therethrough.

5. The device of claim 1 wherein said at least one balloon inflation-deflation lumen comprises a single balloon inflation-deflation lumen extending longitudinally along one side of said catheter body.

6. The device of claim 1 wherein said balloon inflation-deflation aperture comprises a trapezoidal notch formed in said catheter body.

7. The device of claim 1 wherein said balloon inflation-deflation aperture comprises a square notch formed in said catheter body.

8. The device of claim 1 wherein said balloon inflation-deflation aperture comprises:
a generally round, concave main notch formed in said catheter body; and
at least one generally wedge-shaped sub-notch formed in said generally round concave main notch.

9. The catheter device of claim 1 further comprising:
at least one working lumen extending longitudinally through said catheter body.

10. The device of claim 1 wherein said inflatable balloon is configured and constructed of material which will undergo deformation when in its inflated state.

11. The device of claim 10 wherein the material of which said balloon is formed is selected from the group consisting of:
a.) synthetic rubber; and
b.) natural rubber.

12. An angioscope comprising:
a. an elongate, flexible catheter body having a proximal end, a distal end and an outer surface;
b. an inflatable balloon disposed on the outer surface of said catheter body near the distal end thereof;
c. a main working lumen extending longitudinally through said catheter body and having an inner luminal surface and a distal opening through the distal end of said catheter body;
d. a single balloon inflation-deflation lumen extending longitudinally through said catheter body from the proximal end thereof to a point adjacent the location of said balloon;
e. a non-occluding balloon inflation-deflation aperture formed in said catheter body to permit fluidic communication between said balloon inflation lumen and said balloon, said non-occluding balloon inflation aperture comprising at least one wedge-shaped notch cut in the body of said catheter;
f. an endoscopic component passable through the working lumen of said catheter body, said endoscopic component comprising:
i. at least one illumination fiber for transmitting illuminating light from the proximal end of said catheter body to the distal end thereof;
ii. at least one image fiber bundle for transmitting an optical image from the distal end of said catheter body to the proximal end thereof.

13. The angioscope of claim 12 wherein said non-occluding balloon inflation-deflation aperture comprises two(2) wedge-shaped notches cut in the body of said catheter at side-by-side locations.

14. The angioscope of claim 12 wherein said balloon inflation-deflation lumen extends longitudinally along the inner luminal surface of said main working lumen and wherein said balloon inflation-deflation lumen comprises a tube having a wall thickness of 0.002–0.004 inches and an inner luminal diameter of 0.010–0.012 inches and wherein:
each said wedge-shaped notch has a depth from the outer surface of the catheter body to the deepest point of each said notch of 0.006–0.010 inches, thereby providing for fluidic communication between said balloon and said balloon inflation-deflation lumen while precluding passage of balloon inflation fluid from said balloon inflation-deflation lumen into
said main working lumen.

15. The angioscope of claim 14 wherein each said wedgeshaped notch has a depth of approximately 0.008 inches.

16. The angioscope of claim 12 wherein said catheter body has a longitudinal axis extending through the axial center of said catheter body and transverse axes extending perpendicular to said longitudinal axis and through each said wedge-shaped notch, and wherein:
each said wedge-shaped notch is formed at an angle relative to the transverse axis of the catheter body extending through that said wedge-shaped notch.

* * * * *